(12) United States Patent
Moscoso Del Prado et al.

(10) Patent No.: US 9,339,458 B2
(45) Date of Patent: May 17, 2016

(54) USE OF VAGINAL INSULIN SENSITIZING AGENTS

(71) Applicant: ITF RESEARCH PHARMA, S.L.U., Madrid (ES)

(72) Inventors: Jaime Moscoso Del Prado, Madrid (ES); Beatriz Banfi Tosi, Madrid (ES)

(73) Assignee: ITF RESEARCH PHARMA, S.L.U., Madrid (ES)

( * ) Notice: Subject to any disclaimer, the term of this patent is extended or adjusted under 35 U.S.C. 154(b) by 0 days.

(21) Appl. No.: 14/535,810

(22) Filed: Nov. 7, 2014

(65) Prior Publication Data

US 2015/0164788 A1 Jun. 18, 2015

Related U.S. Application Data

(63) Continuation-in-part of application No. 13/201,991, filed as application No. PCT/ES2010/000067 on Feb. 16, 2010, now abandoned.

(30) Foreign Application Priority Data

Feb. 18, 2009 (ES) .................................. 200900448

(51) Int. Cl.
*A61K 31/4439* (2006.01)
*A61K 9/00* (2006.01)
*A61K 31/155* (2006.01)

(52) U.S. Cl.
CPC ............. *A61K 9/0034* (2013.01); *A61K 31/155* (2013.01); *A61K 31/4439* (2013.01)

(58) Field of Classification Search
IPC .......................... A61K 9/0034, 31/153, 31/4439
See application file for complete search history.

(56) References Cited

U.S. PATENT DOCUMENTS

| | | | |
|---|---|---|---|
| 5,874,454 A * | 2/1999 | Antonucci et al. | 514/369 |
| 6,100,300 A * | 8/2000 | Rogosky | 514/635 |
| 6,372,790 B1 * | 4/2002 | Bonhomme et al. | 514/555 |
| 2004/0029784 A1* | 2/2004 | Hathaway | 514/8 |

OTHER PUBLICATIONS

Women's International Pharmacy (2008) 2 pages.*
Healthy Women (2002) 11 pages.*
UNC (The Pharmaceutics and Compounding Laboratory 1996-2015).*
WebbMD enclosed, 2015.*

* cited by examiner

*Primary Examiner* — Shirley V Gembeh
(74) *Attorney, Agent, or Firm* — Cowan, Liebowitz & Latman, P.C.; Mark Montague

(57) ABSTRACT

A method for the treatment and/or prevention of hyperandrogenism and/or polycystic ovary syndrome and/or related disorders comprising the vaginal administration of at least one insulin-sensitizing agent.

14 Claims, 1 Drawing Sheet

USE OF VAGINAL INSULIN SENSITIZING AGENTS

CROSS-REFERENCE TO RELATED APPLICATIONS

This application is a continuation-in-part of application Ser. No. 13/201,991, filed Sep. 15, 2011 in the United States Patent and Trademark Office, which is a national stage of PCT/ES2010/000067, filed Feb. 16, 2010, which claims priority to Spanish Application No. P200900448, filed Feb. 18, 2009, the entire disclosures of each of which are incorporated herein by reference.

FIELD OF THE INVENTION

This invention relates to the use of vaginal insulin sensitising agents for the prevention and/or treatment of hyperandrogenism and/or polycystic ovary syndrome and/or related disorders.

BACKGROUND OF THE INVENTION

In general terms, hyperandrogenism is any clinical or laboratory evidence of an excess of androgens in women. The most frequent clinical evidence of hyperandrogenism in women of childbearing age is hirsutism or acne, with or without anovulation symptoms—such as amenorrhoea or dysfunctional uterine bleeding.

There may be five different causes of hyperandrogenism in women of childbearing potential:
  polycystic ovary syndrome;
  idiopathic hirsutism;
  enzyme deficiencies in the synthesis of steroid hormones;
  androgen-secreting tumours;
  other endocrine disorders such as Cushing's syndrome, etc.

Nevertheless, most women with hyperandrogenism symptoms suffer from polycystic ovary syndrome (80%).

Polycystic ovary syndrome (or PCOS, also called Stein Leventhal syndrome) is a complex metabolic disorder that may lead to changes in the menstrual cycle, cysts in the ovaries, trouble getting pregnant and other health problems. PCOS is the reproductive and hormonal problem that most frequently affects females of reproductive age. It is estimated that approximately 5% of females suffer from this disorder.

According to the American Society for Reproductive Medicine, PCOS is defined by the presence of any two of the following characteristics:
  lack of ovulation over a long period;
  high levels of androgens (hyperandrogenism);
  a large amount of small cysts in the ovaries.

The signs and symptoms of PCOS are related to hyperandrogenism and may include:
  hirsutism, acne and hair loss;
  excess weight or obesity, especially in waist and abdomen;
  irregular, sporadic or lack of menstrual periods;
  larger and/or polycystic ovaries;
  infertility.

Also, females with PCOS are exposed to a higher risk of developing certain health problems, including:
  metabolic syndrome: disorder with several components, amongst which are type 2 diabetes or insulin resistance, high cholesterol levels, high blood pressure (especially around waist and abdomen), high levels of C-reactive protein and high levels of blood coagulation factors;
  excessive thickening of the endometrial lining, abundant or irregular bleeding and endometrial cancer.

PCOS therefore has an important effect on the health system and is a matter of concern for the women who suffer from it.

The pharmacological treatment for hyperandrogenism seeks to correct the associated symptoms by reducing androgen serum levels and/or their peripheral action. This treatment must be maintained for a long time since satisfactory clinical effects usually take months to appear.

Certain drugs approved for the treatment of type 2 diabetes, known as insulin-sensitising agents, have proven to be beneficial in patients with PCOS when are administered by oral route. In this case, the insulin-sensitising agents exert systemic effects that include, among others, the decrease of the body's resistance to insulin by improving the sensitivity of peripheral tissues to said hormone, which finally results in decreased circulating insulin levels and, in parallel, in significantly reduced circulating androgen levels.

Metformin (N,N-dimethylimidodicarbonimidic diamide, Glucophage®), a biguanide-type insulin-sensitising agent, is available for PCOS treatment by oral route. It reduces the clinical signs of hyperandrogenism and improves menstrual irregularities. If metformin alone does not restore ovulation, it may improve a woman's response to pharmaceutical products in fertility treatments. The usual oral dose lies between 500 and 2500 mg/day.

Rosiglitazone (Avandia®) and Pioglitazone (Actos®), belonging to the group of thiazolidindione insulin-sensitising agents, are also available in the United States for PCOS treatment by oral route. Thiazolidindiones have demonstrated reducing hyperandrogenism and restoring ovulation in some patients. The recommended oral dose is between 4 to 8 mg/day for rosiglitazone and between 15 and 30 mg/day for pioglitazone.

SUMMARY OF THE INVENTION

However, insulin-sensitising agents may cause several adverse effects when administered orally, some of which are very serious.

In the case of metformin, the most common, which may cause abandoning the treatment, is gastrointestinal irritation, and occurs in 5 to 20% of cases. Diarrhea is the most common symptom, followed by vomiting, abdominal pain and a bad taste in the mouth. Lactic acidosis is a rare but serious adverse effect of this medicinal product.

In the case of thiazolidindiones, hepatic toxicity is a rare effect that causes much concern. When using these pharmaceutical products, liver function tests must be performed regularly. And its use is not recommended in patients with evidence of liver disease.

During therapy with these pharmaceutical products there may be fluid retention, which may worsen or trigger congestive heart failure. If the patient observes a worsening of heart function, she must stop the treatment.

On the other hand, the use of rosiglitazone has been related to a greater risk of events of myocardial ischaemia. Its use is not recommended in patients with ischaemic cardiopathy and/or peripheral arterial disease.

Cases of occurrence or worsening of diabetic macular edema with decreased visual acuity have also been reported during therapy with these pharmaceutical products.

In women, the risk of long-term fractures associated to therapy with thiazolidindiones must also be considered.

The inventors of this invention have found that, surprisingly, the vaginal administration of insulin-sensitising agents allow reaching adequate levels of the medicinal product in the ovaries, producing local therapeutic effects while significantly reducing systemic exposure, and therefore their adverse effects. Surprisingly, these agents would produce their anti-androgenic effect without requiring indirect systemic action—by increasing the sensitivity of peripheral tissues to insulin—but by direct action on ovarian cells.

In particular, the inventors have observed that the vaginal administration of metformin significantly decreases the plasma levels of testosterone (androgenic hormone). Additionally, they have observed a decrease in the number of atretic (atrophied) follicles in the polycystic ovaries.

Therefore, the vaginal administration of insulin-sensitising agents may be useful in the prevention and/or the treatment of PCOS both in patients with high levels of androgens (due to their effect on the plasma concentration of testosterone) and in patients with normal levels of androgens (due to their direct action on the ovarian tissue, reducing the number of atretic follicles).

Consequently, it may also be useful in the prevention and/or treatment of PCOS related diseases and conditions, such us hirsutism, acne, hair loss, excess weight or obesity—especially in the waist and abdomen-, menstrual irregularities, larger and/or polycystic ovaries and infertility.

It could also be useful in the prevention and/or treatment of other hyperandrogenic conditions (not PCOS) that occur with high plasma levels of androgens, as well as in hyperandrogenism related disorders, such as hirsutism, acne and/or hair loss.

The first aspect of this invention therefore relates to the use of insulin-sensitising agents by vaginal route for the prevention and/or the treatment of polycystic ovary syndrome and/or hyperandrogenic conditions and/or related disorders.

The second aspect relates to pharmaceutical formulations for vaginal administration containing at least one insulin-sensitising agent for the prevention and/or treatment of polycystic ovary syndrome and/or hyperandrogenic conditions and/or related disorders.

The third aspect of this invention relates to a method for preventing and/or treating polycystic ovary syndrome and/or hyperandrogenic conditions and/or related disorders comprising the vaginal administration of a pharmaceutical formulation containing at least one insulin-sensitising agent.

DETAILED DESCRIPTION OF THE INVENTION

Figure 1:
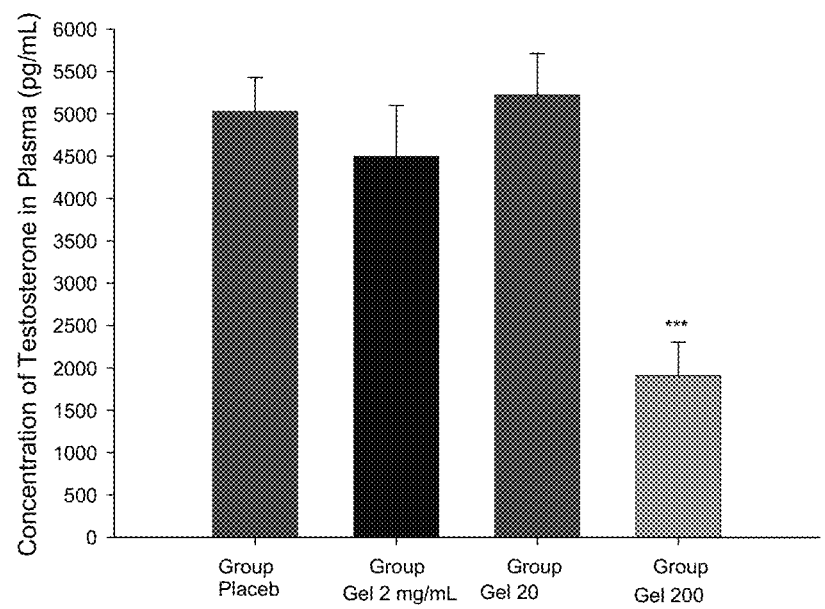
FIG. 1: Concentration of testosterone in plasma.
Figure 2:
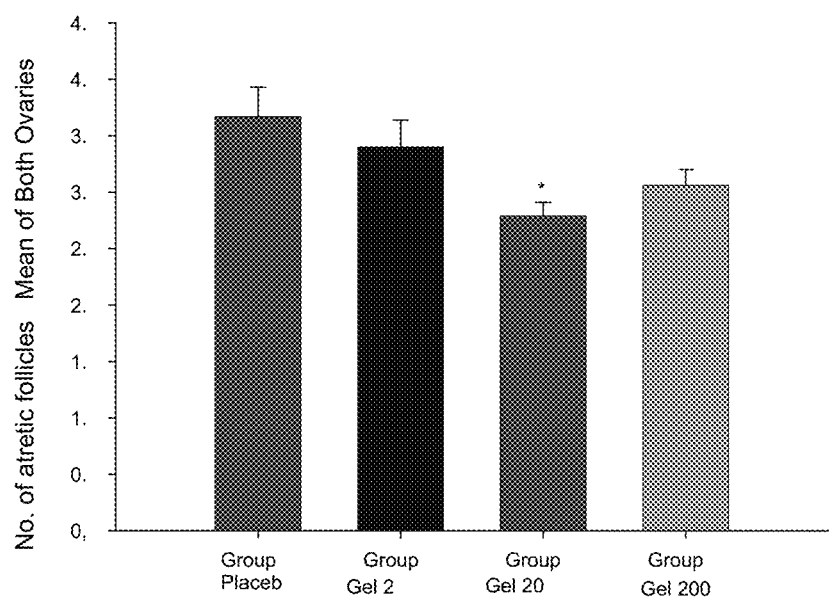
FIG. 2: Mean histological assessment of both ovaries (no. of atretic follicles).

In a particular embodiment, this invention relates to the use of metformin or thiazolidindione by vaginal route in the prevention and/or treatment of polycystic ovary syndrome.

In another particular embodiment, this invention relates to the use of metformin or thiazolidindione by vaginal route in the prevention and/or treatment of other hyperandrogenic conditions with high plasma levels of androgens.

In other embodiments, this invention relates to the use of said pharmaceutical products by vaginal route in the prevention and/or treatment of disorders related with hyperandrogenic conditions, such as hirsutism, acne and/or hair loss.

In another particular embodiment, this invention also relates to the use of said pharmaceutical products by vaginal route in the prevention and/or treatment of disorders related with PCOS, such as hirsutism, acne and/or hair loss, excess weight or obesity—especially in waist and abdomen-, menstrual irregularities, larger and/or polycystic ovaries and infertility.

The formulations of insulin-sensitising agent of this invention can be presented in any dosage form suitable for vaginal administration, for example, as a solid, a semisolid or a fluid.

These formulations will comprise a therapeutically effective and non-toxic amount of at least one insulin-sensitising agent—or one of its pharmaceutically acceptable salts or prodrugs—together with at least one pharmaceutically acceptable excipient. The excipients may be chosen from any of those known by a person skilled in the art and will be suited to the dosage form to be prepared.

The pharmaceutical formulations of this invention may be contained in any device suitable for vaginal administration, for example, a ring or pessary. The materials to be used in the manufacture of the device may be chosen from any of those known by a person skilled in the art that are pharmaceutically acceptable.

The amount of insulin-sensitising agent that must be administered by vaginal use to treat hyperandrogenism and/or PCOS and/or related disorders safely and effectively depends on many factors, including the patient's age and condition, severity of the disease or disorder, frequency of administration of the formulation, etc.

In a particular embodiment, the metformin dose to be administered by vaginal route to treat hyperandrogenism and/or PCOS and/or related disorders will be between 0.01 mg/day and 1000 mg/day; preferably between 0.1 mg/day and 100 mg/day; more preferably between 0.5 and 50 mg/day, and still more preferably between 1 to 10 mg/day.

In another particular embodiment, the metformin dose to be administered by vaginal route will be between 1 to 1000 mg/day; preferably between 10 to 1000 mg/day; more preferably between 50 and 1000 mg/day, and still more preferably between 100 and 1000 mg/day.

Example

The following test illustrates the invention and must not be considered limiting of the scope of the application.

The study objective was to assess the effect of metformin in a non-insulin dependent model for polycystic ovary syndrome (PCOS) induced by dehydroepiandrosterone (DHEA) in rats.

Experimental Method

The formulations to be tested were:
Gels with Metformin at a concentration of 2 mg/mL (FT-147), 20 mg/mL (FT-148) and 200 mg/mL (FT-149).
Gel without Metformin (Placebo; FT-150).
The gels were prepared according to the following formulae:

|  | 2 mg/mL gel (FT-147) | 20 mg/mL gel (FT-148) | 200 mg/mL gel (FT-149) |
| --- | --- | --- | --- |
| Metformin | 0.1 g | 1 g | 10 g |
| Sodium methylparaben | 34.3 mg | 34.3 mg | 34.3 mg |
| Citric acid | 1 g | 1 g | 1 g |
| 40% Sodium hydroxide | q.s. pH = 5.5 approx. | q.s. pH = 5.5 approx. | q.s. pH = 5.5 approx. |
| Natrosol | 0.85 g | 0.85 g | 0.85 g |
| Water | q.s. 50 g | q.s. 50 g | q.s. 50 g |

Female 2-3 weeks-old Sprague-Dawley rats were used.

The animals remained in quarantine for 7 days in the same conditions in which the study was performed. They were weighed as they arrived at the laboratory and every day after that, before the administration of the trial substances and DHEA. The animals average weight during treatment was about 100 g/animal.

They were kept in 255×405×197 mm polycarbonate cages, with sawdust bedding. They were distributed into groups of 5 animals in each cage, chosen at random and were housed in controlled conditions of temperature (22±2° C.), light period (12/12 hr light/darkness), air pressure, number of renewals and relative humidity (30-70%).

They were supplied a standard maintenance diet for rodents and were allowed ad libitum access to drinking water.

Four experimental groups with 8 animals each were used in the study:

Group A: Control=Placebo+DHEA
Group B: Dose 1 Trial Substance (0.016 mg/animal)+ DHEA
Group C: Dose 2 Trial Substance (0.16 mg/animal)+ DHEA
Group D: Dose 3 Trial Substance (1.6 mg/animal)+DHEA Each animal's dose was calculated based on the concentration of each formulation and the administration volume:

Dose 1: formulation of 2 mg/mL with administration of 8 μl/animal=0.016 mg/animal
Dose 2: formulation of 20 mg/mL with administration of 8 μl/animal=0.16 mg/animal
Dose 3: formulation of 200 mg/mL with administration of 8 μl/animal=1.6 mg/animal The trial substance (doses of 0.016, 0.16 and 1.6 mg/animal) and the control substance were administered intravaginally as an aqueous gel at a volume of 8 μl/animal.

The DHEA solution was prepared in a sesame seed oil prior to administration and was injected subcutaneously in a skin fold in the posterior thoracic area (dorsal) at a volume of 0.2 mL.

Administration of the trial or control substance was started on day 0 at the dose specified in point 7.1.

Also on day 0, and immediately after the administration of the trial or control substance, DHEA was administered to each animal by subcutaneous injection (6 mg/100 g body weight/0.2 mL of sesame oil).

This regimen was repeated from day 0 to day 14 (for a total of 15 days of treatment).

Blood samples were obtained from every animal on day 15 (24 hr after the last treatment) by puncture of the abdominal vena cava (anticoagulated with sodium heparin) under anaesthesia (pentobarbital sodium).

Plasma was obtained from each blood sample by centrifugation at 5000 g for 5 minutes, which was frozen for later assessment (quantitative determinations) of testosterone levels by rat-specific commercial immunoassay kits (EIA).

After drawing the blood each animal was sacrificed by cervical dislocation and both ovaries were extracted. These were weighed and fixed in buffered formalin for subsequent histological assessment (by haematoxylin and eosin staining).

Three histological cuts were studied from each ovary, taken from 3 representative areas of each ovary (beginning, centre and end), determining the number of atretic follicles (atrophic). A follicle is considered atretic when one of the following features is observed: pyknosis of the granule cells, granule cells present in follicular fluid, hypertrophy of thecal cells).

Results

A. Concentration of Testosterone in Plasma

Testosterone concentrations in the plasma samples from all animals were determined at the end of the study (Day 15). The results are shown in Table 1:

TABLE 1

Concentration of testosterone in plasma.
Study FCI/07/05/FT - PLASMA LEVELS OF TESTOSTERONE

| GROUP A | | GROUP B | | GROUP C | | GROUP D | |
| --- | --- | --- | --- | --- | --- | --- | --- |
| ANIMAL | TESTOSTERONE (pg/mL) | ANIMAL | TESTOSTERONE (pg/mL) | ANIMAL | TESTOSTERONE (pg/mL) | ANIMAL | TESTOSTERONE (pg/mL) |
| A1 | 3128 | B1 | 2300 | C1 | 6072 | D1 | 2576 |
| A2 | 6164 | B2 | 5474 | C2 | 3450 | D2 | 2622 |
| A3 | 4876 | B3 | 6578 | C3 | 4462 | D3 | 2990 |
| A4 | 3956 | B4 | 2714 | C4 | 3818 | D4 | 736 |
| A5 | 5244 | B5 | 6486 | C5 | 7406 | D5 | 598 |
| A6 | 6670 | B6 | 5336 | C6 | 4554 | D6 | 1518 |
| A7 | 5474 | B7 | 4048 | C7 | 5428 | D7 | 3404 |
| A8 | 4692 | B8 | 3036 | C8 | 6578 | D8 | 828 |
| MEAN | 5025.5 | MEAN | 4496.5 | MEAN | 5221 | MEAN | 1909.000 |

B. Histological Assessment

Three histological cuts were studied from each ovary, taken from 3 representative areas (beginning, centre and end), determining the number of atretic follicles. The results obtained are summarised in Tables 2 to 5:

TABLE 2

Histological assessment of the ovaries of animals in Group A.
Study FCI/07/05/FT - HISTOLOGY
GROUP A

| | NO. OF ATRETIC FOLLICLES LEFT OVARY | | | | NO. OF ATRETIC FOLLICLES Right Ovary | | | Mean Atretic Follicles |
|---|---|---|---|---|---|---|---|---|
| ANIMAL | Cut-off 1 | Cut-off 2 | Cut-off 3 | ANIMAL | Cut-off 1 | Cut-off 2 | Cut-off 3 | Both Ovaries |
| A1 | 2 | 3 | 5 | A1 | 1 | 2 | 3 | 2.67 |
| A2 | 2 | 4 | 5 | A2 | 3 | 6 | 7 | 4.50 |
| A3 | 1 | 7 | 3 | A3 | 3 | 5 | 5 | 4.00 |
| A4 | 2 | 2 | 3 | A4 | 2 | 3 | 3 | 2.50 |
| A5 | 6 | 2 | 2 | A5 | 6 | 5 | 4 | 4.17 |
| A6 | 3 | 3 | 2 | A6 | 3 | 6 | 5 | 3.67 |
| A7 | 1 | 5 | 8 | A7 | 1 | 4 | 6 | 4.17 |
| A8 | 2 | 3 | 5 | A8 | 2 | 4 | 6 | 3.67 |
| | | | | Mean Atretic Follicles Both Ovaries | | | | 3.67 |

TABLE 3

Histological assessment of the ovaries of animals in Group B.
STUDY FCI/07/05/FT - HISTOLOGY
GROUP B

| | No. of Atretic Follicles Left Ovary | | | | No. of Atretic Follicles Right Ovary | | | Mean Atretic Follicles |
|---|---|---|---|---|---|---|---|---|
| ANIMAL | Cut-off 1 | Cut-off 2 | Cut-off 3 | ANIMAL | Cut-off 1 | Cut-off 2 | Cut-off 3 | Both Ovaries |
| B1 | 5 | 4 | 4 | B1 | 2 | 4 | 6 | 4.17 |
| B2 | 3 | 6 | 6 | B2 | 2 | 4 | 2 | 3.83 |
| B3 | 4 | 5 | 3 | B3 | 5 | 5 | 5 | 4.50 |
| B4 | 5 | 4 | 0 | B4 | 2 | 3 | 4 | 3.00 |
| B5 | 3 | 4 | 5 | B5 | 3 | 3 | 2 | 3.33 |
| B6 | 3 | 3 | 4 | B6 | 1 | 2 | 4 | 2.83 |
| B7 | 1 | 3 | 1 | B7 | 2 | 6 | 4 | 2.83 |
| B8 | 1 | 1 | 4 | B8 | 3 | 3 | 4 | 2.67 |
| | | | | Mean Atretic Follicles Both Ovaries | | | | 3.40 |

TABLE 4

Histological assessment of the ovaries of animals in Group C.
STUDY FCI/07/05/FT - HISTOLOGY
GROUP C

| | No. of Atretic Follicles Left Ovary | | | | No. of Atretic Follicles Right Ovary | | | Mean Atretic Follicles |
|---|---|---|---|---|---|---|---|---|
| ANIMAL | Cut-off 1 | Cut-off 2 | Cut-off 3 | ANIMAL | Cut-off 1 | Cut-off 2 | Cut-Off 3 | Both Ovaries |
| C1 | 2 | 2 | 2 | C1 | 4 | 4 | 3 | 2.83 |
| C2 | 2 | 4 | 5 | C2 | 3 | 2 | 2 | 3.00 |
| C3 | 2 | 2 | 2 | C3 | 2 | 4 | 4 | 2.67 |
| C4 | 3 | 3 | 3 | C4 | 2 | 4 | 1 | 2.67 |
| C5 | 2 | 2 | 4 | C5 | 1 | 5 | 4 | 3.00 |
| C6 | 2 | 2 | 5 | C6 | 2 | 3 | 2 | 2.67 |
| C7 | 3 | 3 | 2 | C7 | 1 | 2 | 2 | 2.17 |
| C8 | 2 | 5 | 3 | C8 | 3 | 3 | 4 | 3.33 |
| | | | | Mean Atretic Follicles Both Ovaries | | | | 2.79 |

TABLE 5

Histological assessment of the ovaries of animals in Group D.
STUDY FCI/07/05/FT - HISTOLOGY

| | No. of Atretic Follicles Left Ovary | | | | No. of Atretic Follicles Right Ovary | | | Mean Atretic Follicles |
|---|---|---|---|---|---|---|---|---|
| ANIMAL | Cut-off 1 | Cut-Off 2 | Cut-off 3 | ANIMAL | Cut-off 1 | Cut-off 2 | Cut-Off 3 | Both Ovaries |
| D1 | 2 | 2 | 3 | D1 | 2 | 5 | 5 | 3.17 |
| D2 | 2 | 2 | 3 | D2 | 4 | 5 | 4 | 3.33 |
| D3 | 4 | 4 | 4 | D3 | 3 | 3 | 4 | 3.67 |
| D4 | 2 | 3 | 3 | D4 | 4 | 5 | 3 | 3.33 |
| D5 | 2 | 2 | 4 | D5 | 2 | 1 | 4 | 2.50 |
| D6 | 2 | 4 | 3 | D6 | 1 | 2 | 3 | 2.50 |
| D7 | 3 | 3 | 4 | D7 | 2 | 3 | 3 | 3.00 |
| D8 | 2 | 3 | 3 | D8 | 1 | 4 | 5 | 3.00 |
| Mean Atretic Follicles Both Ovaries | | | | | | | | 3.06 |

CONCLUSIONS

The results demonstrate a very significant reduction of testosterone plasma levels in the animals treated with the trial substance (metformin) at a high dose versus the group treated with the control substance.

A significant reduction was also observed in the number of atretic follicles in the animals treated with the trial substance (metformin) at an intermediate dose versus the group treated with the control substance.

The invention claimed is:

1. A method for the treatment and/or prevention of hyperandrogenism and/or polycystic ovary syndrome and/or related disorders comprising the vaginal administration of metformin or one of its pharmaceutically acceptable salts.

2. The method according to claim 1 for the treatment of polycystic ovary syndrome.

3. The method according to claim 1 for the treatment of hyperandrogenic conditions.

4. The method according to claim 1 for the treatment of hirsutism, acne and/or hair loss related to hyperandrogenic conditions.

5. The method according to claim 1 for the treatment of hirsutism, acne and/or hair loss excess weight or obesity, menstrual irregularities, larger and/or polycystic ovaries and infertility related to polycystic ovary syndrome.

6. The method according to claim 1, wherein the metformin dose ranges between 0.01 mg/day and 1000 mg/day.

7. The method according to claim 6, wherein the metformin dose ranges between 0.1 mg/day and 100 mg/day.

8. The method according to claim 1, wherein the metformin dose ranges between 1 mg/day and 1000 mg/day.

9. The method according to claim 8, wherein the metformin dose ranges between 10 mg/day and 1000 mg/day.

10. The method according to claim 9, wherein the metformin dose ranges between 50 mg/day and 1000 mg/day.

11. The method according to claim 10, wherein the metformin dose ranges between 100 mg/day and 1000 mg/day.

12. The method according to claim 1, wherein the metformin is administered as an aqueous gel.

13. A pharmaceutical formulation for vaginal administration comprising metformin or one of its pharmaceutically acceptable salts for use in the treatment of hyperandrogenism and/or polycystic ovary syndrome and/or related disorders.

14. The method according to claim 13, wherein the at least one insulin-sensitising agent is administered as an aqueous gel.

* * * * *